United States Patent [19]

Radwanski et al.

[11] Patent Number: 4,701,294

[45] Date of Patent: Oct. 20, 1987

[54] EDUCTOR AIRFORMING APPARATUS

[75] Inventors: Fred R. Radwanski, Norcross; Jark C. Lau, Roswell, both of Ga.; James L. Post, Appleton, Wis.

[73] Assignee: Kimberly-Clark Corporation, Neenah, Wis.

[21] Appl. No.: 818,568

[22] Filed: Jan. 13, 1986

[51] Int. Cl.[4] ............................................. B29C 43/22
[52] U.S. Cl. .................................. 264/518; 264/116; 264/121; 425/82.1; 425/83.1
[58] Field of Search ............... 264/115, 116, 121, 517, 264/518; 425/81.1, 82.1, 83.1

[56] References Cited

U.S. PATENT DOCUMENTS

| | | | |
|---|---|---|---|
| 2,931,076 | 4/1960 | Clark | 19/156 |
| 3,268,954 | 8/1966 | Joa | 19/156.3 |
| 3,748,693 | 7/1973 | Jespersen | 19/156.3 |
| 3,777,231 | 12/1973 | Guschin | 264/121 X |
| 3,793,678 | 2/1974 | Appel | 19/156.3 |
| 3,857,657 | 12/1974 | Teed | 425/82.1 |
| 3,863,296 | 2/1975 | Buell | 264/116 X |
| 3,886,629 | 6/1975 | Nakai et al. | 19/156.3 |
| 3,906,588 | 9/1975 | Zafiroglu | 19/156.3 |
| 3,918,126 | 11/1975 | Wood | 19/156.3 |
| 3,973,291 | 8/1976 | Kolbach | 19/148 |
| 4,035,870 | 7/1977 | Reba et al. | 19/155 |
| 4,241,881 | 12/1980 | Laumer | 241/28 |
| 4,264,290 | 4/1981 | Dunkerly, II et al. | 425/83.1 |
| 4,285,647 | 8/1981 | Dunkerly, II | 425/82.1 |
| 4,350,482 | 9/1982 | Alexandrov et al. | 425/83.1 |
| 4,352,649 | 10/1982 | Jacobsen et al. | 425/83.1 |
| 4,375,447 | 3/1983 | Chung | 264/518 |
| 4,375,448 | 3/1983 | Appel et al. | 264/518 |
| 4,388,056 | 6/1983 | Lee et al. | 425/83.1 |

Primary Examiner—Jan H. Silbaugh
Assistant Examiner—Mary Lynn Fertig
Attorney, Agent, or Firm—Paul Yee

[57] ABSTRACT

The present invention provides an improved apparatus and method for forming a fibrous web. In accordance with the invention, a distributor housing delimits a fiberizing zone, and a delivery mechanism supplies a fiberizable material into the fiberizing zone. A moveable striking mechanism located in the fiberizing zone contacts the fiberizable material to initially separate the material into individual fibers. A discharging mechanism exits the fibers from the fiberizing zone into a web forming zone and toward a foraminous web forming layer. A gas delivering mechanism forces a stream of gas into the fiberizing zone to entrain the fibers therein and to eject a moving stream of the gas and fibers through the discharging mechanism into the web forming zone. The gas-fiber stream moves at a velocity sufficient to draw an induced supplementary gas flow past the discharging mechanism and toward the foraminous forming layer. A steering mechanism located in the web forming zone selectively guides the induced supplemental gas flow to direct the fibers toward selected areas of the foraminous forming layer.

13 Claims, 2 Drawing Figures

EDUCTOR AIRFORMING APPARATUS

FIELD OF THE INVENTION

The present invention relates to a method and apparatus for forming a continuous fibrous web. More particularly, the invention relates to a method and apparatus for continuously forming a fibrous web which has a contoured cross-sectional profile.

BACKGROUND OF THE INVENTION

Various products such as disposable diapers, incontinence garments, sanitary napkins and the like include an absorbent fibrous pad as one component. This pad typically has a specific shape and is mass produced from a continuous fibrous web, which has been formed by air-laying fibrous material onto a foraminous forming substrate. Examples of this air-laying technique are described in U.S. Pat. Nos. 2,931,076, issued Apr. 5, 1960 to J. Clark; 3,886,629, issued June 3, 1975 to S. Nakai, et al.; 4,350,482, issued Sept. 21, 1982 to Alexandrov, et al.; and 3,906,588, issued Sept. 23, 1975 to D. Zafiroglu.

Various techniques have been employed to control the thickness or cross-directional profile of the air-layed fibrous web. For example, U.S. Pat. No. 3,748,693, issued July 31, 1973 to P. Jespersen employs a system of plates and moveable vanes to control the deposition of fibers on a foraminous conveyor. U.S. Pat. No. 4,375,448, issued Mar. 1, 1983 to D. Appel, et al. describes a method which provides a full-width feeding of dry fibers to a 2-dimensional flow control and fiber screening system. The system creates substantially no cross-flow forces, and ensures a uniform cross-directional basis weight profile. U.S. Pat. No. 4,375,447, issued Mar. 1, 1983 to R. Chung describes a method for pre-forming and feeding a lightly compacted batt of individualized fibers having a controlled cross-directional profile directly to a rotary fiber orienting and screening mechanism across the full width thereof. The method maintains a controlled cross-directional profile in an air-layed web of dry fibers.

To form a uniform air-layed fibrous web, a method and apparatus described in U.S. Pat. No. 4,285,647, issued Aug. 25, 1981 to C. Dunkerly, II employs a distributor and suction box which are cooperatively constructed and arranged to impart a velocity component to the fibers in the direction of movement of a forming wire. The angle of inclination of the fiber deposition relative to the moving forming wire ranges from about 21°–30°. U.S. Pat. No. 4,264,290, issued Apr. 28, 1981 to C. Dunkerly, II, et al. describes a device which has at least one air turning foil situated upstream from and at the level of the region between a fiber distributor and an underlying moving forming surface. Terminal edge portions of the foils direct ambient air in the direction of the forming surface movement to impart a uniform velocity component in the forming surface movement direction to fibers in transit between the distributor and the forming wire.

The following documents describe systems for blowing gaseously entrained fibers toward a forming surface to produce a nonwoven sheet material. U.S. Pat. No. 4,035,870, issued July 19, 1977 to I. Reba, et al. describes a depositing apparatus which employs a fiber transport means to direct gaseously entrained fibers through a bell former device at a high velocity toward a forming surface positioned adjacent to the outlet of the forming bell. U.S. Pat. No. 4,352,649, issued Oct. 5, 1982 to E. Jacobsen, et al. describes a system for producing nonwoven sheet material which includes compressed air nozzles arranged to force fiber material out of an outlet opening toward a forming surface.

Certain devices have employed stationary projections along an inner wall of a fiberizer and have employed directed gas streams to assist in the forming of individual fibers. For example, U.S. Pat. No. 3,268,954, issued Aug. 30, 1966 to C. Joa describes a device for disintegrating wood pulp board into component fibers and reassembling the fibers having a soft batt. The device disclosed by Joa includes a rotatable drum having an array of picking pins projecting therefrom. The device also has an array of stationary pins projecting toward the picking drum from a wall of a cylinder member that surrounds the drum. A series of air vents are arranged to force the leading ends of the pulp web toward the picking drum. U.S. Pat. No. 4,241,881, issued Dec. 30, 1980 to E. Laumer describes a fiberizer device which includes serrations formed along an interior surface of a hammermill. U.S. Pat. No. 3,918,126, issued Nov. 11, 1975 to D. Wood describes a fiberizer device which includes an air nozzle for directing pressurized air in a stream which strips textile fibers from the surface of a lickerin.

Other devices have employed masks or other types of air flow restricting devices positioned under a forming surface. For example, U.S. Pat. No. 3,973,291, issued Aug. 10, 1976 to C. Kolbach describes a device which employs a masking frame and a sequence of masks which prevent the establishment of partial vacuum through different predetermined sections of a pad-receiving compartment. The device forms discrete, shaped, profile pads.

U.S. Pat. No. 4,388,056 issued July 14, 1983 to F. B. Lee, et al. discloses another apparatus for continuously forming a cyclically contoured and densified air-laid fibrous web. The web has alternatively spaced narrow regions with relatively high basis weight and wide regions with relatively low basis weight. Adjustable shutter plates are configured to span a plurality of transverse plenum segments to modulate the air flow through the device.

Conventional fiberizing devices, such as those described above, have required very large volumes of pumped air to dilute and disperse the fibers, and significant amounts of energy have been required to pump these large volumes of air. The conventional devices have also required complicated mechanisms to form a contoured, profiled pad. For example, these devices have employed complex systems of masks and vanes to regulate the pressure drop across selected portions of a forming surface to thereby control the amount of fibers deposited on those selected portions. As a result, conventional fiberizing devices have been undesirably complicated and expensive to operate.

BRIEF DESCRIPTION OF THE INVENTION

The present invention provides a method and apparatus for forming a fibrous web. Generally stated, the apparatus includes a distributor housing, for delimiting a fiberizing zone, and includes a delivery means for supplying a frangible material into the fiberizing zone. A moveable striking means located in the fiberizing zone contacts the frangible material to initially separate the material into individual fibers. A discharging means exits the fibers from the fiberizing zone into a web forming zone and toward a foraminous web forming layer. A gas delivering means forces a stream of gas into the fiberizing zone to mix with and entrain the fibers therein. This gas delivering means ejects a moving stream of the gas and fibers through the discharging means into the web forming zone. The gas-fiber stream moves at a velocity sufficient to draw a supplementary gas flow past the discharging means and toward the foraminous forming layer. A steering means located in the web forming zone selectively guides the induced supplemental gas flow to direct the fibers toward selected areas of the foraminous forming layer.

The invention further provides a method for forming a fibrous web, which includes the steps of supplying a frangible material into a fiberizing zone and initially separating the material into individual fibers within the fiberizing zone. A stream of gas is forced into the fiberizing zone to entrain the fibers therein and to eject a moving stream of the gas and fibers into the web forming zone. This moving gas-fiber stream has a velocity sufficient to draw a supplementary gas flow into said web forming zone and toward the foraminous forming layer. The supplementary gas flow is also guided to direct the fibers toward selected areas of the foraminous forming layer.

The present invention can advantageously provide a high throughput, high efficiency fiberizer in which the total volume of air required to dilute a gas suspension of fibers is reduced. Since induced air rather than air pumped through a fiberizer mill is employed to dilute the fiber suspension, less energy is required to pump the air. The invention can rapidly dilute and disperse fibers with the flow of induced air, and is capable of forming a contoured pad without employing a complicated mechanism to regulate the pressure drop across selected portions of the forming surface. As a result, when compared to conventional fiberizing and forming devices, the method and apparatus of the present invention can more efficiently produce a nonwoven, airformed web having controlled or selectively varied basis weight contours.

BRIEF DESCRIPTION OF THE DRAWINGS

The invention will be more fully understood and further advantages will become apparent when reference is made to the following detailed description of the invention and the following drawings in which.

DETAILED DESCRIPTION OF THE INVENTION

The method and apparatus of the present invention are useful for forming individual fibers and/or particulates into a nonwoven web. For the purposes of the present invention, the term "fibers" is intended to encompass particulate materials, such as powders, as well as divided, filamentary materials, and blends thereof. The fibers discussed in the present specification and claims may, for example, be composed of cellulosic fibers, synthetic polymeric fibers, particles of superabsorbent materials, or blends of such fibers and particles.

Figure 1:
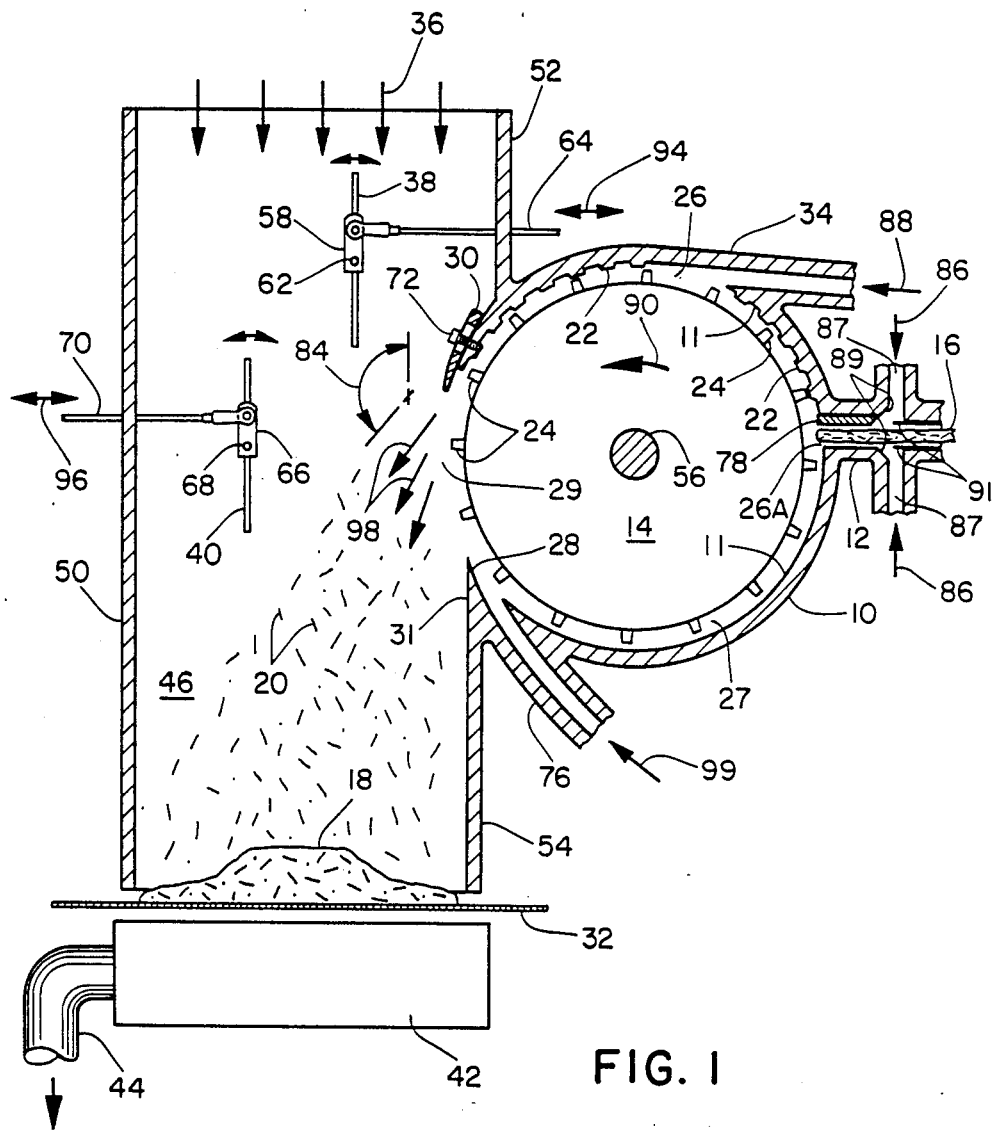
FIG. 1 representatively shows a cross-sectional side elevational view of the apparatus of the invention.
Figure 2:
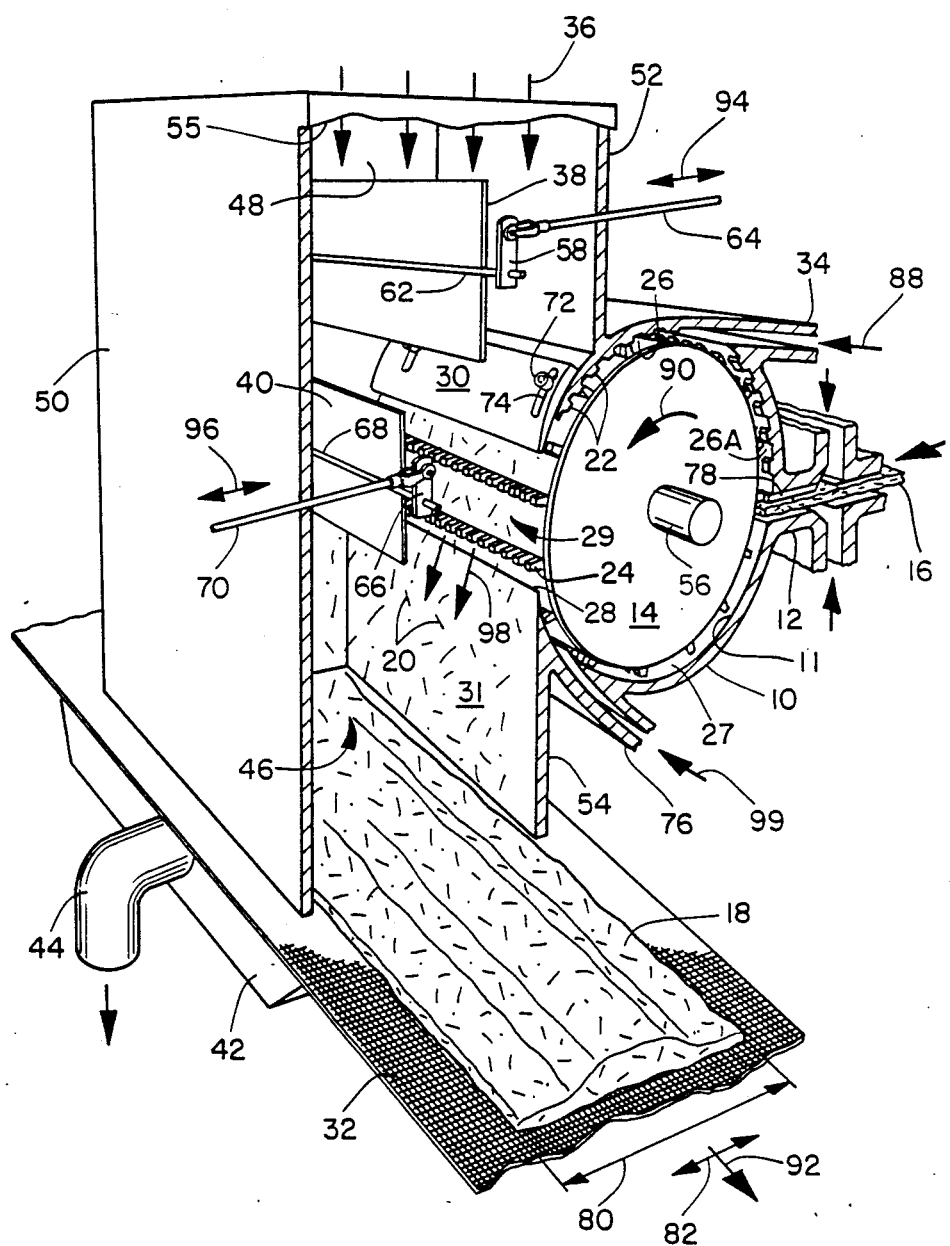
FIG. 2 representatively shows a perspective view of the apparatus of the invention in which one wall has been removed for clarity.

With reference to FIGS. 1 and 2, a representative apparatus for forming a fibrous web 18 includes a distributor housing 10 which delimits a fiberizing zone 26, 26A therein. Delivery means, such as inlet channel 12, supplies a frangible material 16 into the fiberizing zone. A movable striking means, such as hammer elements on rotatable drum 14, is located in the fiberizing zone 26A to contact the fiberizable material and to initially separate the material into discrete, individual fibers (or particles). Discharging means, which comprises edge members that define a discharge opening 29 therebetween, exits the fibers from the fiberizing zone, into a web forming zone 46, and toward a foraminous web forming layer 32. Gas delivering means, such as gas inlet conduit 34, forces a stream of gas into fiberizing zone 26 along a selected path, which has a directional component that is substantially tangential to a moveable surface of the striking means. The gas delivered stream mixes and merges with the fibers to convey the fibers through distributor housing 10, and eject a rapidly moving stream of gas and fibers through the discharging means into the web forming zone 46. The moving gas-fiber stream has a velocity sufficient to induce a supplementary gas flow 36 through web forming zone 46, past the discharging means, and toward foraminous forming layer 32. Steering means, such as steering vanes 38 and 40, are located in web forming zone 46 to selectively guide the induced supplementary gas flow 36 and direct the fibers toward selected areas of foraminous forming layer 32.

In the shown embodiment, distributor housing 10 is generally cylindrical in shape, and includes an essentially cylindrical side wall member and two essentially circular end plate members. The cylindrical wall member includes an inwardly facing wall surface 11, and the wall and end plate members define a generally enclosed cylindrical volume.

Delivery conduit 12 guides a frangible material 16 to the interior of housing 10, and the material is delivered from a suitable source, such as a supply roll (not shown). The interior end of delivery conduit 12 includes an anvil member 78 positioned at interior wall surface 11. This anvil member provides a wear resistant impact surface that supports frangible material 16 during the fiberization process.

In a particular aspect of the invention, a flow of gas is directed by conducting means into the region of anvil 78. More particularly, a flow of anvil air 86 is directed into supply conduit 12 through conduits 87, which are positioned above and/or below the anvil. These gas flows pressurize supply conduit 12 and reduce the amount of fibers that might be recirculated out of distributor housing 10 through this conduit.

Anvil air 86 also helps to maintain material 16 in a desired position relative to anvil 78 for efficient fiberization. To more effectively direct the anvil air through conduit 12 and into annular space 27, the downstream, terminal end portions of conduits 87 are selectively contoured, for example, with beveled edges 89 and extending members 91. The contoured edges are angled or turned towards housing 10, as illustrated in FIG. 1, to direct the flow of anvil air toward the housing.

In the illustrated embodiment, the moveable striking means comprises a generally cylindrical hammer drum 14 which is rotatable about axle 56 in the direction indicated by arrow 90. In the shown embodiment, axle 56 is oriented approximately parallel to the movement direction 92 of web forming layer 32. This configuration can advantageously be employed to produce a web 18 having a contoured cross-sectional profile which is thicker at its medial portion than at its marginal edge portions. Hammer drum 14 may also be arranged with axle 56 oriented non-parallel to movement direction 92. Such a configuration can be employed to produce a more uniform thickness profile across the cross-direction of web 18. A plurality of protuberances or hammer elements 24 extend radially outward from the outer peripheral surface of the hammer drum and are arranged in a selected pattern array. For example, in the shown embodiment, the hammer elements are arranged in generally straight lines along the axial length of the hammer drum. Other arrays, such as curvilinear alignments, may also be employed. The hammer drum is located substantially coaxial with housing 10, and is sized to provide a radial clearance between the drum and the housing. As a result, the drum and housing define an annular space 27 therebetween.

A discharge opening 29 extends through the side wall of housing 10 and opens into a web forming zone 46. In the shown embodiment, discharge opening 29 is generally rectangular in shape and is delimited by a leading edge member 30 and a trailing edge member 28. These leading and trailing edge members are oriented transverse to the movement direction of the hammer drum. Preferably, the edge members are oriented substantially perpendicular to the drum movement direction and have their length dimensions aligned essentially parallel to the axis of the hammer drum.

Leading edge member 30 is preferably adjustable to provide improved performance. More particularly, the leading edge member operably controls the fiber deposition trajectory 98. In the shown embodiment, leading edge member 30 includes a pair of substantially parallel slots 74 which extend circumferentially with respect to housing 10. Attachment screws 72 extend through the slots 74 and engage suitable threaded holes located in the wall member of housing 10. This particular configuration allows a selective positioning of leading edge member 30 along the circumferential direction relative to housing 10. This selective circumferential positioning can be employed to adjust the size of discharge opening 29 and to adjust the discharge angle 84 at the leading edge of the gas-fiber stream that is ejected out from annular fiberizing zone 26 through discharge opening 29.

Trailing edge member 28 is constructed and arranged such that its radially outward surface 31, relative to housing 10, is positioned along a plane which is substantially tangential to the movement of hammer elements 24 at discharge opening 29. This tangential positioning is important because it operates to reduce turbulent, recirculating gas flows and currents which could cause undesired fiber distribution patterns, such as fiber clumping or flocculation, on the foraminous forming layer 32. In the shown embodiment, trailing edge member 28 is positioned such that its outward surface 31 is aligned along a generally vertical plane that is located substantially tangential to the circular, rotational movement of hammer elements 24 as they pass by the axially extending, circumferential centerline of discharge opening 29.

The discharge opening 29 should be substantially free of obstructions, such as screens and baffles. Obstructions at the discharge opening can restrict the exit, deflect the trajectories of fibers moving from the housing, and undesirably recirculate the fibers through annulus 27 with hammer drum 14.

Web forming zone 46 is defined and delimited by a front wall 48, side walls 50, 52, 54 and a back wall 55. Back wall 55 is sectioned away from FIG. 2 for the purposes of clarity. As illustrated in the Figures, the walls form an open ended chamber or conduit through which the fiberized material is directed toward a foraminous forming layer 32. The top of the forming chamber is open to the ambient atmosphere, and the bottom of the chamber opens onto the foraminous forming layer.

Foraminous forming layer 32 is positioned at the bottom of web forming zone 46, and typically comprises a foraminous wire mesh. The forming layer is moveable in a direction generally indicated by arrow 92, and this movement transports the formed fibrous web 18 out from the web forming zone 46 for subsequent processing. It will be readily appreciated that the speed of the movement of forming layer 32 and the movement of material 16 can be adjusted to regulate the thickness of the formed fibrous web 18.

Gas delivery conduit 34 extends through the wall of housing 10 and opens into fiberizing zone 26 through a slot opening that extends axially along the wall of the fiberizer housing. A suitable pressurizing means (not shown) forces a housing gas stream 88 into fiberizing zone 26 through the inlet slot. This stream of gas mixes with and entrains the fibers located within the fiberizing zone, and also operates to transport the fibers through housing 10 and to forcibly eject a rapidly moving stream of gas and fibers through discharge opening 29 into web forming zone 46. The moving gas-fiber stream is provided with a velocity sufficient to educe or draw an induced, supplementary gas flow 36 into the top of the web forming zone. The supplementary gas flow joins with gas-fiber stream 98, and travels past discharge opening 29 toward foraminous forming layer 32. To better accomplish these effects, the stream of gas 88 injected into fiberizing zone 26 should have a velocity component which is substantially circumferentially tangential to the cylindrical periphery of hammer drum 14. In a particularly advantageous aspect of the invention, gas delivery conduit 34 forcibly injects a stream of gas into housing 10 along a path which is substantially totally tangential to the moveable, peripheral, outer surface of hammer drum 14. With such a configuration, essentially all of the injected gas stream moves along a path that is substantially co-directional with the movement direction of the hammer elements on hammer drum 14. This arrangement more efficiently utilizes the full force and velocity of the injected gas stream 88 to produce the gas-fiber 98 stream and control the supplementary gas flow 36.

Steering means comprised of steering vanes 38 and 40 are located within web forming zone 46 to selectively guide the induced supplemental gas flow 36. More particularly, the vanes guide and deflect selected portions of the induced supplemental gas flow, and the movement of the deflected gas flow operably directs greater amounts of fibers toward selected areas along the transverse cross direction 82 of the foraminous forming layer.

In the shown embodiment, steering vane 38 is pivotable about shaft 62 and is generally rectangular in shape. It will be readily appreciated, however, that other steering vane shapes, such as oval or dog bone shapes, may also be employed. A control arm 58 extends radially away from shaft 62 and connects to actuator rod 64. The actuator rod is movable along the directions indicated by arrow 94 and operably rotates steering vane 38 about shaft 62 to selected positions. Similarly, steering vane 40 is pivotable about shaft 68. A second control arm 66 extends radially away from shaft 68 and connects to a second actuator rod 70. Actuator rod 70 is moveable in the directions indicated by the arrows 96 and operably rotates steering vane 40 about shaft 68 to a selected position. By appropriately setting the rotational positions of vanes 38 and 40, the apparatus can be adjusted to produce a desired cross-sectional profile within fibrous web 18. The particular rotational position of the vanes will depend on the desired gas-fiber stream trajectory 98 and on the desired contour of web 18. For example, the steering vanes can be adjusted to produce a fibrous web having a humped, transverse profile wherein the web thickness at the longitudinal center line of the web is greater than the web thickness at the two lateral, side edges of the web.

In another aspect of the invention, a gas jetting means comprised of gas jet conduit 76 directs a gas flow 99 into the annular space 27 between house 10 and hammer drum 14. This stripper gas jet moves in a direction that is generally opposite and counter to the rotational direction of the hammer drum. In addition, this gas jet is directed generally tangential to the outer periphery of hammer drum 14, and is introduced into annular space 27 at a location adjacent to the edge of discharge opening 29 that is defined by trailing edge member 28. Thusly configured, the gas jet directed through conduit 76 operates to reduce the recirculation of fibers and heated air through distributor housing 10. This heated air is generated during the fiberization and the high velocity transport processes within housing 10. Limiting the recirculation of the heated air advantageously helps to reduce the temperature within the housing.

In still another aspect of the invention, fiberizer housing 10 includes an array of protuberances 22 located on and distributed along at least a portion of the inwardly facing wall surface 11. Protuberances 22 contact the fibers that have been initially fiberized between hammer elements 24 and anvil 78. This contact assists in separating the material and further ensures the break-up and dispersion of the material into discrete, individual fibers.

During operation, a suitable driving means, such as an electric motor (not shown), rotates hammer drum 14 about shaft 56 at an angular velocity that produces a circumferential, peripheral speed of at least about 30 meters per second at hammer elements 24. Preferably, the peripheral speed of the hammer elements ranges from about 80–165 meters per second, and more preferably ranges from about 90–130 meters per second to provide improved fiberization of material 16.

The moving hammer elements 24 impact frangible material 16 as the material is fed through conduit 12 into annular space 27. This impact initially separates material 16 into fibers and propels the fibers along the direction of the hammer element movement. The moving fibers impact against protuberances 22, and these protuberances assist in the process of separating the fiberizable material into individual, discrete fibers. Concurrently, the movements of hammer elements 24 continue to propel the fibers through fiberizing zone 26 in the direction of the hammer drum rotation.

A stream of pressurized gas 88 is injected through conduit 34 at a speed which is approximately equal to or greater than the tip speed of the hammer elements extending from drum 14. The injected, housing gas stream moves circumferentially through fiberizing zone 26 and exits out of housing 10 into web forming chamber 46 through discharge opening 29. The force and velocity of the injected gas stream entrains and carries fibers 20 therewith, and ejects a stream of gas and fibers through discharge opening 29 in the direction generally indicated by the arrows 98.

The high speed movement of the gas fiber stream educes or draws a supplementary gas flow 36 into the top of web forming zone 46. This supplementary gas flow diffuses the gas-fiber stream and expands the volume of the gas-fiber stream. In particular, the supplemental gas flow expands the dimension of the gas-fiber stream that corresponds to the transverse width dimension 80 of fibrous web 18. The width of web 18 can, for example, be up to about 0.5 m. The apparatus of the invention is particularly advantageous because it can produce a rapid expansion of the gas-fiber stream over a relative short distance without causing the formation of undesired fiber distribution patterns.

A vacuum or suction box 42 is positioned beneath foraminous forming layer 32, and a suitable pumping means (not shown) draws a flow of gas through foraminous forming layer 32 through vacuum box 42 and out through conduit 44. The gas flow through conduit 44 is adjusted to maintain a mass balance of gas flow through web forming zone 46. In other words, the volume amount of gas drawn out through conduit 44 is substantially equal to the total volume amount of gas introduced by the gas-fiber stream and by the educed supplementary gas flow 36. In a preferred embodiment of the invention, suction box 42 maintains a pressure within forming chamber 46 that is below the ambient atmospheric pressure. With such a configuration, there is less dusting and blowing of stray fibers out of the forming chamber into the surrounding environment.

The distinctive configuration provided by the present invention advantageously widens and increases the operating "window" of the device. As a result, the method and apparatus of the invention can operate without being excessively sensitive to the amount of gas forced through delivery conduit 34 and ejected out of distributor housing 10 into forming chamber 46. The method and apparatus of the present invention are also less sensitive to the amount of vacuum produced within vacuum box 42. The vacuum need not be tightly controlled to produce the desired configuration of fibrous web 18.

A further advantage provided by the present invention is that the air-to-fiber ratios within the fiberizing zones of distributor housing 10 can be reduced. As a result, the device can operate with greater efficiency.

The stripper jet 99 of gas, which is forced through conduit 76 into annular space 27, further improves the efficiency of the device. Since this stripper gas jet moves in a direction counter to the rotation of hammer drum 14 and since it is positioned adjacent to trailing edge member 28, the gas jet can assist in removing fibers from hammer drum 14 and directing the gas-fiber stream 98 out of housing 10 through discharge opening 29. This operation reduces the amount of fibers and hot air that may undesirably be recirculated through annular space 27 back into fiberizing zone 26.

The following examples are provided to give a more detailed understanding of the invention. The particular materials, proportions and parameters are exemplary, and are not intended to specifically limit the scope of the invention.

EXAMPLES 1-2

An airforming apparatus was constructed in accordance with the present invention, and had the rotational axis of the hammer drum oriented substantially parallel with the machine direction 92 of foraminous web forming layer 32. The hammer drum was rotated to provide a hammer tip speed of approximately 328 ft/sec (100 m/sec), and the discharge opening through the housing 10 was axially aligned substantially parallel with the hammer drum rotational axis. The discharge opening had a opening gap width, measured along the circumferential direction, of approximately 2.75 in. The steering vanes 38 and 40 were aligned perpendicular to the web forming layer, and the top of the forming chamber 46 was open to the ambient atomosphere. The distance between the discharge opening and the web forming layer was about 18 in.

For the experiments of Examples 1 and 2, the apparatus was operated under the particular conditions set forth in Table 1.

TABLE 1

| Conditions | Example 1 | Example 2 |
| --- | --- | --- |
| Pulp Throughput Rate (pounds per inch of machine width per hour) | 167 | 133 |
| Anvil Air (cfm/inch of machine width) | 4 | 3 |
| Tangential, Housing Air (cfm/inch of machine width) | 15 | 17 |
| Stripper Air (cfm/inch of machine width) | — | 3 |
| Induced Supplemental Air (cfm/inch of machine width) | 90 | 149 |
| Clearance of Hammer Element Tip from Housing Inner Wall | ⅛ in | ⅛ in | cfm = ft³/min
"Machine width" corresponds to the axially extending lengths of the hammer mill drum and the discharge opening in the hammer drum housing.
The two anvil air inlet openings each measured 3/16 in × 22 in.
The tangential, housing air inlet opening measured ½ in × 22 in.
The stripper air inlet opening measured 1 in × 22 in.
The forming chamber measured 12 in in the cross direction (82) and 22 in in the machine direction (92).

The fibrous webs formed in Examples 1 and 2 were contoured and measured 12 in. in width. With respect to the cross direction of the web, the center of each web had a 2:1 basis weight profile as compared to the two side edges of each web. That is, there was approximately twice as much web material in the center 4in of the web as there was in the two remaining 4in wide edge portions located on each side of the web center portion.

Having thus described the invention in rather full detail, it will be appreciated that various changes and modifications can be made, all of which are contemplated as being within the scope of the invention as defined by the subjoined claims.

What is claimed is:

1. An apparatus for forming a fibrous web, comprising:
   a. a distributor housing which delimits a fiberizing zone;
   b. delivery means for supplying a frangible material into said fiberizing zone;
   c. rotatable striking means located in said fiberizing zone for contacting said material within said fiberizing zone to initially separate said material into individual fibers, said striking means having an axis of rotation and having an outer peripheral surface which is moveable along a selected rotational direction;
   d. discharging means for exiting said fibers from said fiberizing zone, into a web forming zone and toward a foraminous web forming layer, said forming layer being moveable along a direction approximately parallel to said striking means axis of rotation;
   e. gas delivering means for forcing a stream of housing gas into said fiberizing zone, said zone delimited so as to cause said stream of housing gas to entrain said fibers therein and to eject a moving stream of said gas and fibers through said discharging means into said web forming zone, said stream of, housing gas having a velocity component which is substantially tangential to and co-directional with said rotational direction of said striking means peripheral surface, said ejected gas-fiber stream having a velocity sufficient to draw an induced supplementary gas flow past said discharging means and toward said foraminous forming layer, and said supplementary gas flow arranged to expand said gas-fiber stream across a transverse, width dimension of said forming layer; and
   f. steering means located in said web forming zone for selectively deflecting said induced supplemental gas flow to join with said gas-fiber stream and thereby direct said fibers toward selected areas along the transverse, width dimension of said foraminous forming layer to form a fibrous web having a contoured cross-sectional profile along the transverse, width dimension of the fibrous web.

2. An apparatus as recited in claim 1, further comprising an array of protuberances located on an inwardly facing wall surface of said distributor housing and extending into said fiberizer zone for contacting said initially fiberized material to assist in separating said material into individual fibers.

3. An apparatus as recited in claim 1, wherein said gas delivering means is constructed and arranged to force said stream of gas into said fiberizing zone along a path which is substantially tangential to a moveable peripheral surface of said moveable striking means.

4. An apparatus as recited in claim 1, further comprising vacuum means for drawing a flow of gas from said web forming zone and through said web forming layer.

5. An apparatus as recited in claim 1, wherein said discharging means comprises:
   a. an adjustable leading edge member arranged transverse to the movement direction of said striking means, said leading edge member capable of being selectively positioned to adjust a discharge angle at a leading edge of the gas-fiber stream ejected from said distributor housing; and
   b. a trailing edge member, which is arranged transverse to the movement direction of said striking means and which cooperates with said leading edge member to define a discharge opening therebetween, said trailing edge member having a surface that is positioned along a plane that is substantially tangential to a peripheral surface of said striking means.

6. An apparatus as recited in claim 1, further comprising conducting means for directing a gas flow into said frangible material delivery means.

7. An apparatus as recited in claim 1, further comprising a stripper jet conduit located adjacent to said discharging means for directing a stripper gas flow which removes fibers from said striking means.

8. An apparatus as recited in claim 1, wherein said gas delivering means forces said stream of housing gas to provide the tangential velocity component thereof with a speed which is approximately equal to or greater than a tip speed of hammer elements extending from said striking means.

9. A method for forming a fibrous web, comprising the steps of:
 a. delimiting a fiberizing zone with a distributor housing;
 b. supplying a frangible material into said fiberizing zone with delivery means;
 c. contacting said fiberizable material with rotatable striking means located in said fiberizing zone to initially separate said material within said fiberizing zone into individual fibers, said striking means having an axis of rotation and having an outer peripheral surface which moves along a selected rotational direction;
 d. exiting said fibers with discharging means from said fiberizing zone, into a web forming zone and toward a foraminous web forming layer;
 e. moving said forming layer along a direction approximately parallel to said striking means axis of rotation;
 f. forcing a stream of housing gas into said fiberizing zone with gas injection means to entrain said fibers within said gas stream and to eject a moving stream of said gas and fibers through said discharging means into said web forming zone, said stream of housing gas having a velocity component which is substantially tangential to and co-directional with the rotational direction of said striking means peripheral surface, said ejected gas-fiber stream having a velocity sufficient to induce a supplementary gas flow past said discharging means and toward said foraminuous forming layer, said said supplementary gas flow arranged to expand said gas-fiber stream across a transverse, width dimension of said forming layer; and
 g. selectively deflecting said induced supplemental gas flow with adjustable steering means located in said web forming zone to join with said gas-fiber stream and thereby direct said fibers toward selected areas along the transverse, width dimension of said foraminous forming layer to form a fibrous web having a selected, contoured cross-sectional profile along the transverse, width dimension of the fibrous web.

10. A method as recited in claim 9, further comprising the step of directing a gas flow into said frangible material delivery means.

11. A method as recited in claim 9, further comprising the step of removing fibers from said striking means with a stripper jet gas flow located adjacent to said discharging means.

12. A method as recited in claim 9, wherein said fibers are selectively directed to form a contoured fibrous web.

13. A method as recited in claim 9, wherein said forcing step (f) provides the tangential velocity component of said stream of housing gas with a speed which is approximately equal to or greater than a tip speed of hammer elements extending from said striking means.

* * * * *